(12) United States Patent
Wang et al.

(10) Patent No.: US 8,101,788 B2
(45) Date of Patent: Jan. 24, 2012

(54) SILICON PRECURSORS AND METHOD FOR LOW TEMPERATURE CVD OF SILICON-CONTAINING FILMS

(75) Inventors: Ziyun Wang, Allen, TX (US); Ashutosh Misra, Plano, TX (US); Ravi Laxman, San Jose, CA (US)

(73) Assignee: Air Liquide Electronics U.S. LP, Houston, TX (US)

( * ) Notice: Subject to any disclaimer, the term of this patent is extended or adjusted under 35 U.S.C. 154(b) by 1102 days.

(21) Appl. No.: 11/695,379

(22) Filed: Apr. 2, 2007

(65) Prior Publication Data

US 2008/0081106 A1 Apr. 3, 2008

Related U.S. Application Data

(60) Provisional application No. 60/827,472, filed on Sep. 29, 2006.

(51) Int. Cl.
*C07F 7/04* (2006.01)
*C07F 7/08* (2006.01)
*C07F 7/10* (2006.01)

(52) U.S. Cl. ......... 556/410; 556/431; 556/434; 556/435

(58) Field of Classification Search ........................ None
See application file for complete search history.

(56) References Cited

U.S. PATENT DOCUMENTS

| | | | |
|---|---|---|---|
| 2004/0138489 | A1 | 7/2004 | Wang et al. |
| 2004/0146644 | A1 | 7/2004 | Ziao et al. |
| 2005/0080285 | A1 | 4/2005 | Wang et al. |

OTHER PUBLICATIONS

Kirilin et al., {(Chloromethyl)alkoxysilanes, silethanes, and silethenes in the synthesis of linear and heterocyclic compounds, Russian Journal of General Chemistry (2005), 75(9), 1402-1405}.*
Rakhlin et al., {Organosilicon Derivatives of 1,1-Dimethylhydrazine: Novel Precursors of Thin-Film Dielectric Coatings, Doklady Chemistry (Translation of the chemistry section of Doklady Akademii Nauk) (2003), 388(4-6), 47-49}.*
He et al., {X-ray Crystal and Molecular Structures of Bis(2-methylhydrazino)tetraphenyldisiloxane: Linear at Oxygen, Planar vs Pyramidal at Nitrogen, Organometallics (1994), 13(6), 2496-2499}.*
Wannagat et al., {Chemistry of silicon-nitrogen compounds. XCVIII. New reactions of 1,3-dichlorodisilazanes and 1,3-dichlorodisiloxanes, Monatsh. Chem. (1971), 102(6), 1844-50}.*
Wannagat et al., Silicon-nitrogen compounds. LXI. Silicon-hydrazine compounds. 11. Hypergolity of silylhydrazines, Monatshefte fuer Chemie (1966), 97(4), 1157-62}.*
Sergeeva et al., {Addition reaction of methylbis(1,1-diethylhydrazino)silane and acetylene, Huaxue Xuebao (1964), 30(1), 77-8}.*
International Search Report for PCT/IB2007/053987.
Chemical Abstracts Service, Columbus, Ohio, 2003. Rakhlin, V.I. et al. "*Organosilicon derivatives of 1,1-dimethylhydrazine: Novel precursors of thin-film dielectric coatings.*" Database accession No. 139:133607.
Chemical Abstracts Service, Columbus, Ohio, 1963. Wannagat, U. et al. "*Chemistry of silicon-nitrogen compounds. XCVIII. New reactions of 1,3-dichlorodisilazanes and 1,3-dichlorodisiloxanes.*" Database accession No. 76:85873.
Chemical Abstracts Service, Columbus, Ohio, 1958. Sergeeva, Z.I. et al. "*Reaction of nonsymmetric dialkylhydrazines with alkylchlorosilanes.*" Database accession No. 59:55161.
Chemical Abstracts Service, Columbus, Ohio, 1958. Wannagat, U. et al. "*Reaction of diphenyldichlorosilanes with hydrazine.*" Database accession No. 53:50902.
Written Opinion for related PCT/IB2007/053987, Feb. 25, 2008.

* cited by examiner

*Primary Examiner* — Kamal Saeed
*Assistant Examiner* — Michael Barker
(74) *Attorney, Agent, or Firm* — Patricia E. McQueeney

(57) ABSTRACT

Novel silicon precursors for low temperature deposition of silicon films are described herein. The disclosed precursors possess low vaporization temperatures, preferably less than about 500° C. In addition, embodiments of the silicon precursors incorporate a —Si—Y—Si— bond, where Y may comprise an amino group, a substituted or unsubstituted hydrocarbyl group, or oxygen. In an embodiment a silicon precursor has the formula:

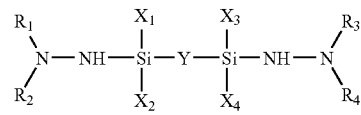

where Y is a hydrocarbyl group, a substituted hydrocarbyl group, oxygen, or an amino group; $R_1$, $R_2$, $R_3$, and $R_4$ are each independently a hydrogen group, a hydrocarbyl group, a substituted hydrocarbyl group, a heterohydrocarbyl group, wherein $R_1$, $R_2$, $R_3$, and $R_4$ may be the same or different from one another; $X_1$, $X_2$, $X_3$, and $X_4$ are each independently, a hydrogen group, a hydrocarbyl group, a substituted hydrocarbyl group, or a hydrazino group, wherein $X_1$, $X_2$, $X_3$, and $X_4$ may be the same or different from one another.

2 Claims, No Drawings

SILICON PRECURSORS AND METHOD FOR LOW TEMPERATURE CVD OF SILICON-CONTAINING FILMS

CROSS-REFERENCE TO RELATED APPLICATIONS

This application claims priority to U.S. provisional application Ser. No. 60/827,472, filed on Sep. 29, 2006 and incorporated herein by reference.

BACKGROUND

1. Field of the Invention

This invention relates to generally to the formation of silicon films. More specifically, the invention relates to silicon precursors for low temperature deposition of silicon films.

2. Background of the Invention

Silicon-containing dielectric deposition is commonly used in the fabrication of integrated circuits. For example, silicon nitride can be used in semiconductor devices as diffusion barriers, gate insulators, in trench isolation and capacitor dielectrics. Low temperature chemical vapor deposition (CVD) is one of the widely used methods in the semiconductor industry for silicon-containing film fabrication.

In the fabrication of devices, a thin passive layer of a chemically inert dielectric material such as, silicon nitride is required. This layer functions as diffusion masks, oxidation barriers, intermetallic dielectric material with high dielectric breakdown voltages and passivation layers. Typically, the nitride films are used as side wall spacers in the memory devices and, with oxides, oxynitrides, as well as gate dielectrics for the transistors.

The most commonly used precursor in semiconductor manufacture for silicon nitride growth is bis(tertiary-butylamino silane) (BTBAS), which requires high temperature (>600° C.) in the chemical vapor deposition processes in order for forming high quality silicon nitride films. This high temperature process temperature requirement is incompatible with the next generation integrated circuit (IC) device manufacturing, where deposition temperature of below 500° C. is desired. Other popular precursors used for silicon film application include dichlorosilane, hexachlorodisilane and ammonia. But these precursors still are problematic. For example, silane and dicchlorosilane are pyrophoric, meaning these compounds may spontaneously ignite at high temperatures and form toxic gases. In addition, films manufactured from dichlorosilane may contain contaminants, such as chlorine and ammonium chloride.

Consequently, there is a need for silicon precursor compounds having a low vaporization temperature and an acceptable film deposition rate that do not have the associated problems with present precursor compounds.

BRIEF SUMMARY

Novel silicon precursors for low temperature deposition of silicon films are described herein. The disclosed precursors possess low vaporization temperatures, preferably less than about 500° C. In addition, embodiments of the silicon precursors incorporate a —Si—Y—Si— bond, where Y may comprise an amino group, a substituted or unsubstituted hydrocarbyl group, or oxygen. Further aspects and embodiments of the invention are described in more detail below.

These and other needs in the art are addressed in one embodiment by a silicon precursor having the formula:

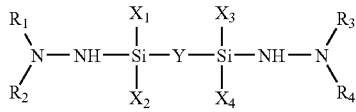

wherein Y is a hydrocarbyl group, a substituted hydrocarbyl group, oxygen, or an amino group; $R_1$, $R_2$, $R_3$, and $R_4$ are each independently a hydrogen group, a hydrocarbyl group, a substituted hydrocarbyl group, a heterohydrocarbyl group, wherein $R_1$, $R_2$, $R_3$, and $R_4$ may be the same or different from one another; $X_1$, $X_2$, $X_3$, and $X_4$ are each independently, a hydrogen group, a hydrocarbyl group, a substituted hydrocarbyl group, or a hydrazino group, wherein $X_1$, $X_2$, $X_3$, and $X_4$ may be the same or different from one another.

In another embodiment, a silicon precursor comprises a disilazane substituted with at least two hydrazino groups. In a further embodiment, a silicon precursor comprises a disiloxane substituted with at least two hydrazino groups.

In one embodiment, a method of forming a silicon-containing film on a substrate comprises providing a precursor having the formula:

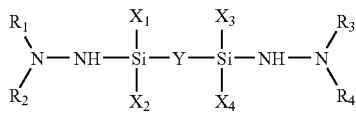

wherein Y is a hydrocarbyl group, a substituted hydrocarbyl group, oxygen, or an amino group; $R_1$, $R_2$, $R_3$, and $R_4$ are each independently a hydrogen group, a hydrocarbyl group, a substituted hydrocarbyl group, a heterohydrocarbyl group, wherein $R_1$, $R_2$, $R_3$, and $R_4$ may be the same or different from one another; $X_1$, $X_2$, $X_3$, and $X_4$ are each independently a hydrogen group, a hydrocarbyl group, a substituted hydrocarbyl group, a heterohydrocarbyl group, or a hydrazino group, wherein $X_1$, $X_2$, $X_3$, and $X_4$ may be the same or different from one another. The method further comprises vaporizing the precursor to form a vapor. In addition, the method comprises contacting the substrate with the vapor so as to form the silicon-containing film on the substrate.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

DETAILED DESCRIPTION

Generally, embodiments of the novel silicon precursor comprise a compound having the formula:

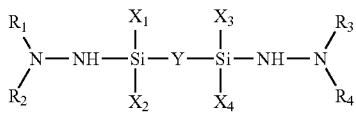

In one embodiment, Y comprises any hydrocarbyl group, for example, substituted or unsubstituted hydrocarbyl groups. The term "hydrocarbyl" as defined herein refers to any functional group comprising exclusively of carbon and hydrogen atoms. Example include without limitation, alkyl groups, alkenyl groups, alkynyl groups, aryl groups, or combinations thereof. Specific examples of alkyl groups include without limitation methyl, ethyl, propyl, butyl, etc. In addition, the hydrocarbyl groups may be branched or substituted hydrocarbyl groups such as secondary or tertiary alkyls. As used herein, "substituted hydrocarbyl" means a branched or substituted functional group containing exclusively hydrogen and carbon atoms. The hydrocarbyl groups preferably comprise 1 to 6 carbon atoms. However, Y may comprise hydrocarbyl groups with any number of carbon atoms.

In a particular embodiment, the silicon precursor comprises a disilazane. That is, Y comprises a nitrogen containing group having the formula N-Z where Z comprises a hydrogen group or a hydrocarbyl group. Example of suitable hydrocarbyl groups include alkyl groups such as without limitation, $-CH_3$, $-CH_2CH_3$, $-CH(CH_3)_2$ or $-C(CH_3)_3$. However, Z may comprise any suitable hydrocarbyl group. In embodiments, Z comprises hydrocarbyl groups having from 1 to 7 carbon atoms. Nevertheless, Z may comprise hydrocarbyl groups with any number of carbons. In other embodiments, the silicon precursor comprises a disiloxane where Y is an oxygen atom.

$R_1$, $R_2$, $R_3$, and $R_4$, are, in general, hydrocarbyl groups or hydrogen groups. Examples of suitable hydrocarbyl groups include without limitation, alkyl groups, alkenyl groups, alkynyl groups, aryl groups, or combinations thereof. $R_1$, $R_2$, $R_3$, and $R_4$, typically comprise hydrocarbyl groups having 1 to 7 carbon atoms. However, $R_1$, $R_2$, $R_3$, and $R_4$, may comprise any suitable functional group such as a heterohydrocarbyl group. As defined herein, a "heterohydrocarbyl" is a hydrocarbyl group additionally containing nitrogen or oxygen. The heterohydrocarbyl group may or may not be substituted or branched. Examples of suitable heterohydrocarbyl groups include without limitation, $-OCH_3$ and $-N(CH_3)_2$. $R_1$, $R_2$, $R_3$, and $R_4$, may each comprise the same functional group or different functional groups. In a preferred embodiment, $R_1$ comprises the same functional group as $R_3$ and $R_2$ comprises the same functional group as $R_4$.

In other embodiments, $R_1$, $R_2$, $R_3$, and $R_4$, each may comprise a cyclic functional group such as without limitation, a heterocyclic group, a cycloalkyl group having from 3 to 6 carbon atoms (i.e. a $C_3$-$C_6$ cyclic group), a benzyl group, or combinations thereof In one embodiment, $R_1$, $R_2$, $R_3$, and $R_4$, each form a heterocyclic ring with N as shown in the following structure:

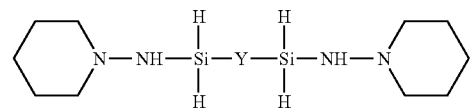

The heterocyclic ring may comprise from 2 to 6 carbon atoms. In addition, other functional groups may be attached to the heterocyclic ring.

In some embodiments, $X_1$, $X_2$, $X_3$, and $X_4$ may each comprise hydrocarbyl groups, respectively, such as an alkyl group, an alkenyl group, an alkynyl group, an aryl group, or combinations thereof In other embodiments, $X_1$, $X_2$, $X_3$, and $X_4$ may each comprise hydrogen, respectively. Additionally, $X_1$, $X_2$, $X_3$, and $X_4$ may each comprise a heterohydrocarbyl group such as without limitation, an alkylamino or a dialkylamino group. However, it is contemplated that $X_1$, $X_2$, $X_3$, and $X_4$ may comprise any suitable functional group.

In a preferred embodiment, $X_1$, $X_2$, $X_3$, and $X_4$ may independently comprise hydrazino groups with the formula:

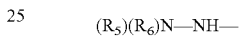

where $R_5$ and $R_6$ comprise the same functional groups as applied to $R_1$, $R_2$, $R_3$, and $R_4$, described above. $R_5$ and $R_6$ may comprise the same functional group or different functional groups. In an embodiment, $R_5$ and $R_6$ may bond with each other to form a cyclic functional group.

In some embodiments, $X_1$, $X_2$, $X_3$, and $X_4$ comprise the same hydrazino groups. For example, in an embodiment, the silicon precursor may comprise the following formula:

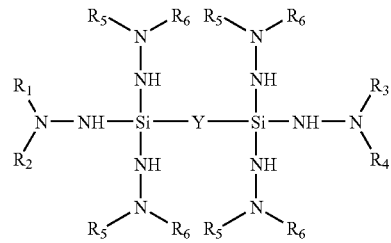

where $R_5$ and $R_6$ all comprise the same functional group. In a further embodiment, $X_1$, $X_2$, $X_3$, and $X_4$ comprise the same hydrazino group, as shown in the structure above, and $R_1$, $R_2$, $R_3$, $R_4$, $R_5$ and $R_6$ all comprise the same functional group. In other words, each Si atom in the $-Si-Y-Si-$ group would be bonded to three identical hydrazino groups.

However, in other embodiments, $X_1$, $X_2$, $X_3$, and $X_4$ comprise different hydrazino groups. That is, even though $X_1$ and $X_3$ both comprise hydrazino groups, the $R_5$ and $R_6$ groups for each respective hydrazino group may comprise different functional groups, $R_5$ and $R_6$. Likewise, $X_1$ and $X_2$ may comprise different hydrazino groups and $X_3$ and $X_4$ may comprise different hydrazino groups.

In preferred embodiments, the silicon precursor is symmetric. In other words, the substituents for each Si atom are symmetrically distributed in relation with the $-Si-Y-Si-$ group. Without limitation, examples of symmetric embodiments are shown below:

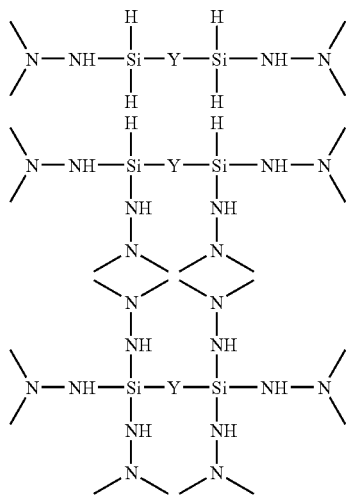

It is envisioned that the disclosed silicon precursors may comprise all isomers of the various embodiments described herein. In other embodiments, the silicon precursor is asymmetrical. In other words, the functional groups substituted on each Si atom in the —Si—Y—Si— bond may not be identical. In addition, the functional groups for each Si atom may be arranged differently. For illustrative purposes only, an embodiment of an asymmetrical silicon precursor is shown below:

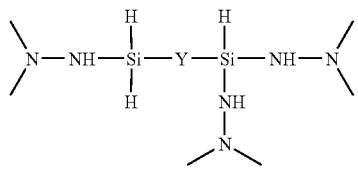

Embodiments of the disclosed silicon precursor and its derivatives are characterized by a vaporization temperature of less than 500° C. Moreover, the disclosed compounds may deposit thin film at less than 550° C., preferably less than 500° C., more preferably less than 450° C. The silicon-containing films that are formed with embodiments of the silicon precursor may be used to form high k gate silicates, and silicon epitaxial films.

In a further embodiment, a method of depositing silicon film on a substrate comprises providing one or more of the disclosed silicon precursors. Providing the silicon precursor may entail introducing one or more of the disclosed silicon precursors into a reaction chamber. Other reactants may be introduced into the reaction chamber. For example, ammonia may be introduced along with the silicon precursor. Examples of other reactants that may be introduced include without limitation, hydrazine, amines, or combinations thereof. The reaction chamber may be of any configuration known to one of skill in the art. Examples of suitable reactors that may be used in conjunction with the disclosed precursors include without limitation, vertical tube reactors, horizontal tube reactors, hot wall reactors, cold wall reactors, barrel reactors, etc.

In an embodiment, the silicon precursor is diluted with an inert gas. Any suitable inert gas may be used such as Ar, He, N, or combinations thereof. Alternatively, one or more of the reactants are dissolved in a solvent to form a solution. According to one embodiment, the reactants or the solution may then be vaporized and reacted to form a vapor or a gas.

In an embodiment, a chemical reaction is initiated by the application of heat. Heat may be applied by any suitable means such as without limitation, thermal, convection, induction, conduction, plasma, etc. The reactants are vaporized at a temperature preferably at a temperature less than about 500° C., more preferably at a temperature less than about 450° C. The vapor is then allowed to diffuse on to a substrate. In general, the substrate is a wafer. Other examples of substrates include without limitation, SiC. The vapor contacts and adsorbs on to the substrate depositing the silicon film on the substrate. In other embodiments, the deposition of thin films using the disclosed precursors involves atomic layer deposition which is also well known in the art.

The aforementioned method is only one embodiment for which the disclosed silicon precursor may be utilized. In additional embodiments, the described silicon precursors may be used in processes such as plasma enhanced chemical vapor deposition, low pressure chemical vapor deposition, plasma-enhanced chemical vapor deposition, ultrahigh vacuum chemical vapor deposition, and atomic layer deposition. Other processes for which embodiments of the silicon precursor may be used include processes for depositing silicon-containing films such as silicon oxide, silicon oxynitride, or silicon nitride.

In another embodiment, a method of making a silicon precursor comprises the following reaction:

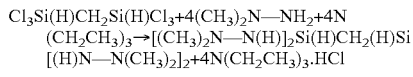

In an additional embodiment, a method of making a silicon precursor comprises the following reactions:

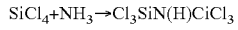

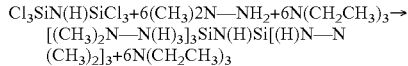

While embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:
1. A silicon precursor having the formula:

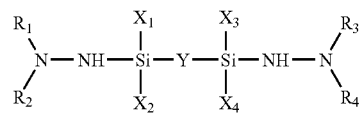

wherein Y is a hydrocarbyl group, a substituted hydrocarbyl group, oxygen, or an amino group; $R_1$, $R_2$, $R_3$, and $R_4$ are each a hydrocarbyl group, a substituted hydrocarbyl group, or a heterohydrocarbyl group; $X_1$, $X_2$, $X_3$, and $X_4$ are each a hydrazino group having the formula $(R_5)(R_6)N$—NH— where $R_5$ and $R_6$ are a hydrocarbyl group, a substituted hydrocarbyl group, or a heterohydrocarbyl group, and wherein $R_1$ to $R_6$ are all the same function group.

2. A silicon precursor having the formula:

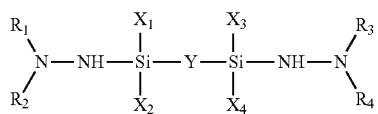

wherein Y is a hydrocarbyl group, a substituted hydrocarbyl group, oxygen, or an amino group; $R_1$, $R_2$, $R_3$, and $R_4$ are each independently a hydrogen group, a hydrocarbyl group, a substituted hydrocarbyl group, a heterohydrocarbyl group, wherein $R_1$, $R_2$, $R_3$, and $R_4$ may be the same or different from one another; $X_1$, $X_2$, $X_3$, and $X_4$ are each a hydrogen group.

* * * * *